(12) United States Patent
Jinnouchi

(10) Patent No.: US 9,554,876 B2
(45) Date of Patent: Jan. 31, 2017

(54) RECTANGULAR ORTHODONTIC ARCH WIRE APPLIANCE AND MANUFACTURING METHOD OF RECTANGULAR ORTHODONTIC ARCH WIRE APPLIANCE

(71) Applicant: Hiroshi Jinnouchi, Yokohama (JP)

(72) Inventor: Hiroshi Jinnouchi, Yokohama (JP)

(*) Notice: Subject to any disclaimer, the term of this patent is extended or adjusted under 35 U.S.C. 154(b) by 80 days.

(21) Appl. No.: 14/066,624

(22) Filed: Oct. 29, 2013

(65) Prior Publication Data

US 2015/0118634 A1 Apr. 30, 2015

(51) Int. Cl.
*A61C 3/00* (2006.01)
*A61C 7/20* (2006.01)
*A61C 7/12* (2006.01)

(52) U.S. Cl.
CPC . *A61C 7/20* (2013.01); *A61C 7/12* (2013.01); *A61C 2201/007* (2013.01); *Y10T 29/49838* (2015.01)

(58) Field of Classification Search
CPC ............... A61C 7/12–7/34; A61C 2201/007; Y10T 29/49838
USPC ...................................... 433/8–24
See application file for complete search history.

(56) References Cited

U.S. PATENT DOCUMENTS

| | | | | |
|---|---|---|---|---|
| 4,192,070 A | * | 3/1980 | Lemchen | A61C 7/30 433/11 |
| 6,276,932 B1 | * | 8/2001 | Jinnouchi | A61C 7/20 433/20 |
| 8,550,814 B1 | * | 10/2013 | Collins | A61C 7/12 433/17 |
| 2012/0148974 A1 | * | 6/2012 | Chester | A61C 7/02 433/20 |
| 2012/0322019 A1 | * | 12/2012 | Lewis | A61C 7/28 433/10 |
| 2014/0154637 A1 | * | 6/2014 | Hansen | A61C 7/20 433/20 |
| 2014/0272760 A1 | * | 9/2014 | Cameron | A61C 7/20 433/20 |

* cited by examiner

*Primary Examiner* — Matthew Nelson
(74) *Attorney, Agent, or Firm* — Yokoi & Co., U.S.A.; Toshiyuki Yokoi

(57) ABSTRACT

A connecting wire is a wire having a circular cross-section and made of shape memory alloy or the like. Individual blocks have a cross-section configured to engage with an orthodontic bracket and have a through hole to insert the connecting wire. Because a torque is applied separately to each of the individual blocks after the connecting wire and individual blocks are formed according to an arch form on a Monson sphere, the torque can be applied keeping a three-dimensional curve such as the Monson sphere.

6 Claims, 20 Drawing Sheets

F I G . 8
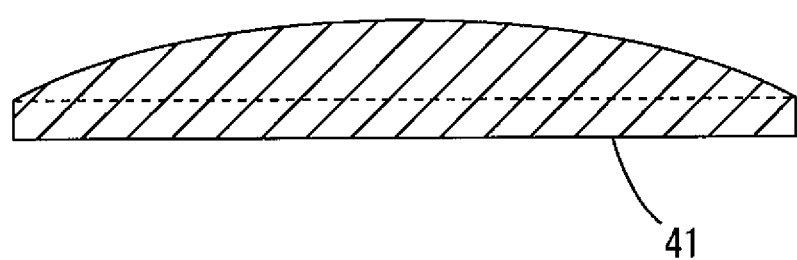

F I G . 1 1
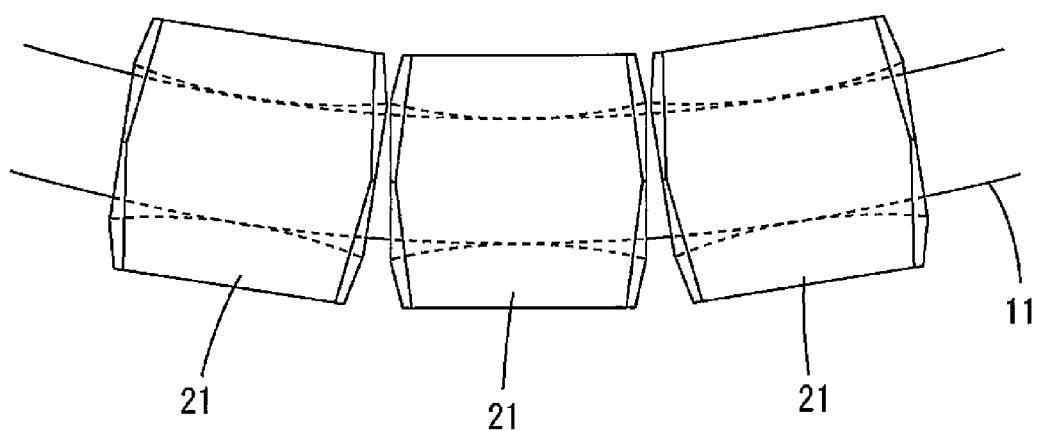

FIG.14

|  | shape memory alloy block | non shape memory alloy block |
|---|---|---|
| shape memory alloy wire | △ | ◎ |
| non shape memory alloy wire | ◎ | △ | arch wire

RECTANGULAR ORTHODONTIC ARCH WIRE APPLIANCE AND MANUFACTURING METHOD OF RECTANGULAR ORTHODONTIC ARCH WIRE APPLIANCE

BACKGROUND OF THE INVENTION

1. Field of the Invention

The present invention relates to a rectangular orthodontic arch wire appliance and a manufacturing method of the rectangular orthodontic arch wire appliance.

2. Description of the Related Art

In the conventional full-banded orthodontic treatment, only aesthetic aspects were emphasized when preparing an arch wire (rectangular arch wire). Therefore, respective teeth were arranged flatly in an elevational view and the arch wire was bent along a dental arch in a plan view.

FIG. 18 shows a conventional arch wire in a plan view. FIG. 19 shows the conventional arch wire in a side view. The left side of the figures is the front of the arch wire.

As explained later, an occlusal surface of the dental arch is not originally flat. As shown by two-dot chain line in FIG. 19, the occlusal surface is curved slightly in an anteroposterior direction. However, respective teeth are initially arranged flatly as shown by solid line.

The teeth are arranged flatly not only for the aesthetic aspects, but also for applying a torque to the arch wire.

FIG. 20 is a rear view of the conventional arch wire. As shown in the figure, in order to give a twisting power to the arch wire, the arch wire should be twisted. If the arch wire is not flat, a shape of the arch wire in a plan view is changed when the rectangular arch wire is twisted.

On the other hand, U.S. Pat. No. 6,276,932 discloses a technology based on a need of such a three-dimensional shape.

BRIEF SUMMARY OF THE INVENTION

In the conventional treatment, respective teeth were arranged flatly, and therefore an original three-dimensional shape could not be kept.

The present invention provides a rectangular orthodontic arch wire appliance and a manufacturing method of the rectangular orthodontic arch wire appliance capable of applying an orthodontic treatment keeping the original three-dimensional shape.

In the present invention, the "Monson spherical plate" means a substantially spherical plate member having a spherical surface corresponding to a curve of the occlusal surface of the dental arch or having a part of the spherical surface. Theoretically, the curve of the occlusal surface is called a Monson curve. Therefore, in the present invention, an imaginary spherical surface containing the Monson curve is called a "Monson sphere" and a plate having a shape of the Monson sphere is called a "Monson spherical plate". However, the above definitions do not have to be strictly applied and a diameter or a size of the Monson curve is suitably specified according to the condition of the teeth of a patient to be treated.

Meanwhile, the theoretical "Monson curve" is defined as "a kind of a compensating curve derived from the spherical theory of jaw movement proposed by G. S. Monson and forms a spherical surface of 8 inch diameter (1 inch is approximately 2.54 cm)", ENCYCLOPAEDIA DENTALIS, Jul. 20, 1976 first Edition, Nagasue Shoten, page 703. The explanation continues as follows: "Actually, at first, a compensating curve is formed on an occlusion rim using a clock glass or the like made of metal and having a diameter of 8 inch. The compensating curve forms a part of a spherical surface and the center of the compensating curve is located at the glabella (ethmoid crista galli). A set of artificial teeth is arranged so that incisal margin and both buccolingual cusps contact the spherical surface. By arranging the set of artificial teeth as described above, in case of complete denture, balanced occlusion can be realized so that the artificial teeth move along the condyle path when the mandible moves" (ibid). The sphere theory of Monson is "the theory of an imaginary jaw movement publicized by Monson in 1920" (ibid). The explanation continues as follows: "In a well-grown mandible, condyles, incisal margin of anterior teeth and buccolingual side cusps of molar teeth are arranged on a sole spherical surface, and a mandibular movement is performed as a sliding movement along the spherical surface. It is said that the long axis of each tooth is directed to the center of the sphere, the center of the sphere is lying on a median line of the body and in the ethmoid crista galli, and the radius is 4 inch on an average" (ibid).

One aspect of the present invention is comprised of a connecting wire having a circular cross-section; and individual blocks having a cross-section configured to engage with an orthodontic bracket and having a through hole to insert the connecting wire, wherein the individual blocks can be fixed to the connecting wire in advance by inserting the connecting wire into the individual blocks.

According to the present invention, the connecting wire having the circular cross-section are preliminarily inserted into the individual blocks, then a three-dimensional curve is formed to be fit along a Monson spherical plate, and then the individual blocks are fixed according to a necessary torque. By adopting the above configuration, each of the individual blocks can be separately twisted on the connecting wire as needed. In other words, only the individual blocks are twisted and the connecting wire having the circular cross-section is not twisted. When applying a torque to the individual blocks, the individual blocks rotates sliding on a contact surface of the connecting wire, and the connecting wire is fixed not to be moved. Even if the connecting wire forms a three-dimensional curve to be fit along the Monson spherical plate, an entire shape of the orthodontic arch wire appliance in a plan view is not changed when the individual blocks are twisted because each of the individual blocks are twisted separately on the connecting wire. A shape engageable with the orthodontic bracket is, for example, a polygonal shape.

In another aspect of the present invention, the individual blocks are formed to be narrower toward a lingual side so that two neighboring individual blocks do not interfere with each other when the connecting wire is inserted into the individual blocks and the connecting wire is bent along a dental arch.

In another aspect of the present invention, the individual blocks are formed to be narrower toward a labial or buccal side in a same manner as the lingual side.

In another aspect of the present invention, the connecting wire is made of shape memory alloy.

In another aspect of the present invention, the individual blocks are made of shape memory alloy.

In another aspect of the present invention, the connecting wire having the circular cross-section is inserted into the individual blocks in advance, a three-dimensional curve is formed according to an arch curve on a Monson sphere, a torque is applied to the individual blocks, and the individual blocks are fixed on the connecting wire.

In another aspect of the present invention, the connecting wire is formed to be three-dimensionally curved along the Monson spherical plate.

In another aspect of the present invention, neighboring individual blocks are located at a distance so that the connecting wire can be warped.

In addition, as a manufacturing method of an orthodontic arch wire appliance, the orthodontic arch wire appliance can be manufactured by inserting a connecting wire having a circular cross-section into individual blocks; forming a three-dimensional curve according to an arch curve on a Monson sphere so that the individual blocks can engage with an orthodontic bracket; applying a torque to the individual blocks; and fixing the individual blocks on the connecting wire.

BRIEF DESCRIPTION OF THE DRAWINGS

FIG. 8 is a cross-sectional view of a convex Monson spherical plate.

FIG. 11 is a schematic diagram showing interference between neighboring individual blocks when the connecting wire is bent.

FIG. 14 is a chart showing a combination of materials of the connecting wire and the individual blocks, selecting from a material using shape memory alloy and a material using non shape memory alloy.

DETAILED DESCRIPTION OF THE INVENTION

Hereafter, embodiments of the present invention will be explained with reference to the drawings.

Figure 1:
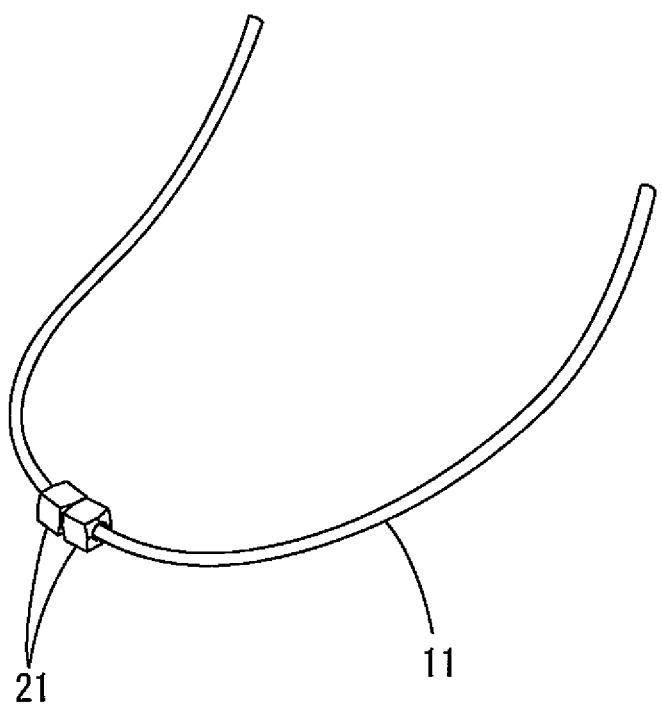
FIG. 1 is a perspective view showing a basic structure of an orthodontic arch wire appliance.
Figure 2:
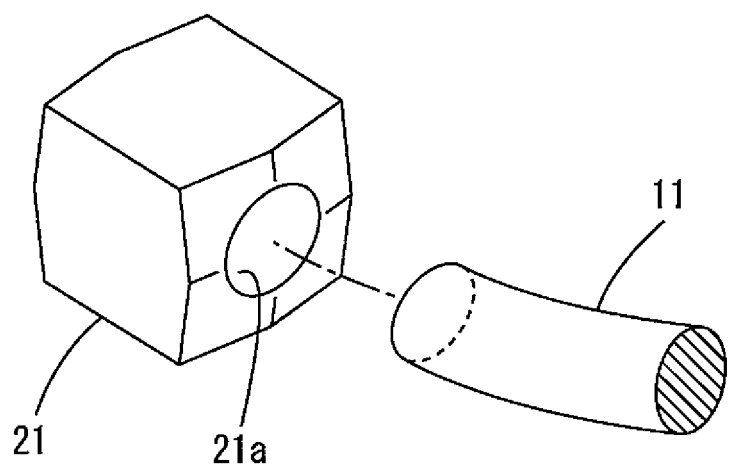
FIG. 2 is an enlarged perspective view showing an essential portion of the basic structure of the orthodontic arch wire appliance.

FIG. 1 is a perspective view showing a basic structure of an orthodontic arch wire appliance concerning an embodiment of the present invention. FIG. 2 is an enlarged perspective view showing an essential portion of the basic structure of the orthodontic arch wire appliance.

In the figures, a connecting wire 11 is a wire whose cross-section is circular (hereafter called as a circular cross-section). The connecting wire is made of, for example, shape memory alloy. The connecting wire is bent in three dimensions (width direction: X, depth direction: Y, and height direction: Z) on the later mentioned Monson spherical plate so as to be fit along a dental arch of a patient. Meanwhile, the individual block 21 has a polygonal cross-section to engage with the later mentioned orthodontic bracket, and has a through hole 21a to insert the connecting wire 11. A plurality of individual blocks 21 are individually fixed to the connecting wire 11. Although only two individual blocks 21 are drawn in FIG. 1 for the convenience of understanding, a necessary number of individual blocks 21 are used in practice to cover almost the whole connecting wire 11. The connecting wire 11 as a whole, to which the individual blocks 21 are inserted, can be a substitute for the conventional rectangular arch wire.

Figure 3:
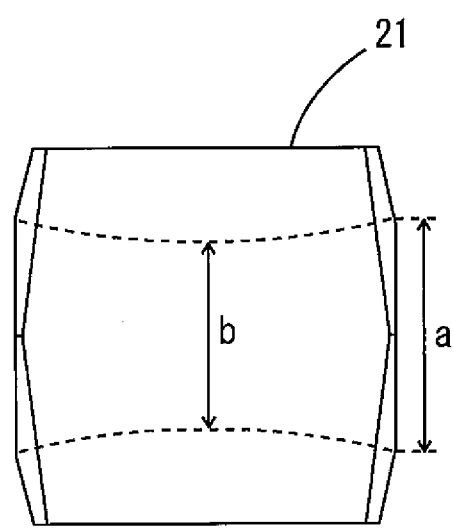
FIG. 3 is a plan view of an individual block.
Figure 4:
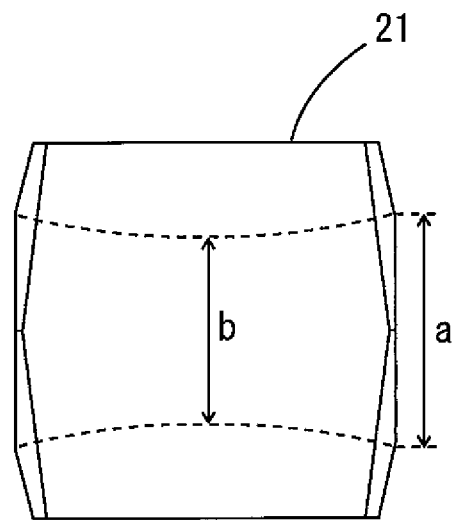
FIG. 4 is a front view of the individual block.
Figure 5:
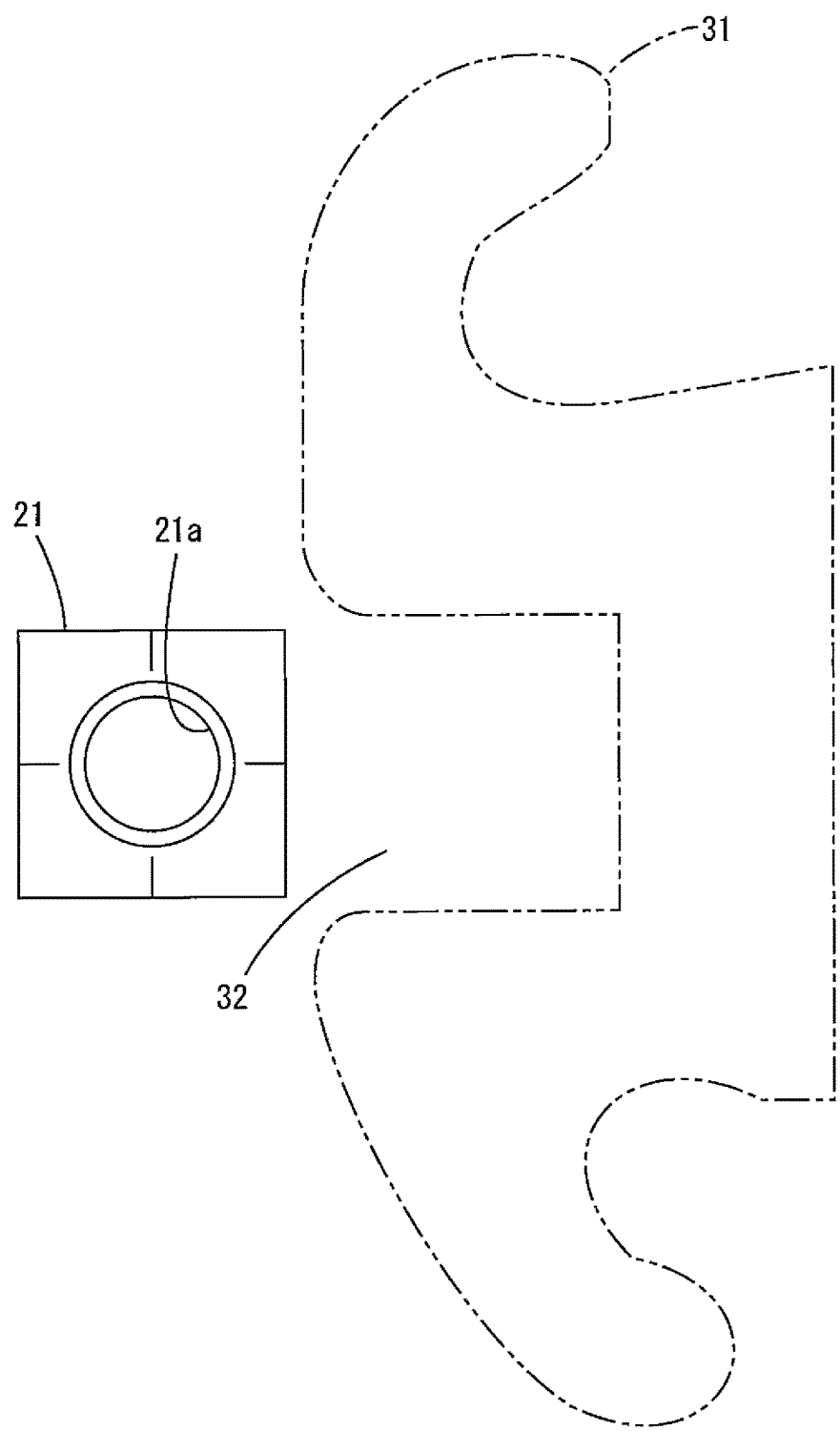
FIG. 5 is a side view of the individual block.

FIG. 3 shows the individual block 21 in a plan view, FIG. 4 shows in a front view, and FIG. 5 shows in a side cross sectional view.

The individual block 21 has an approximately cubic shape, but corners of both side surfaces are slightly chamfered. Consequently, the individual block 21 has a hexagonal shape when viewed from the top, the bottom, the front, or the rear. In other words, width is maximum at the center in a longitudinal direction and narrower at a front end or a rear end. Also, width is maximum at the center in a vertical direction and narrower at a top end or a bottom end.

Although the corners of both side surfaces are chamfered in the present embodiment, the edges of both side surfaces can be chamfered instead. Alternatively, both side surfaces can be slightly conical. Because both side surfaces have an opening of the through hole 21a, width is maximum at an edge of the opening.

An inner diameter of the through hole 21a is maximum at both side surfaces as shown as "a" in the figures, the inner diameter becomes gradually smaller toward the center, and the inner diameter is minimum at the center as shown as "b" in the figures. By adopting the above structure, the connecting wire 11 can be warped in the through hole 21a when the connecting wire 11 is bent. Therefore, whole the orthodontic arch wire appliance can be easily bent.

Each edge of the individual block 21 is chamfered to be rounded as much as possible so as to be smoothly inserted into the later mentioned orthodontic bracket.

When the connecting wire 11 is inserted into the individual blocks 21 and bent along the dental arch, two neighboring individual blocks 21 interfere with each other if the width is constant in a longitudinal direction. To "interfere" means that two neighboring individual blocks 21 are contacted at a point on an inner side while a space is formed at an outside. However, because the individual blocks 21 are formed to be narrower toward a side of the dental arch, the interference between two neighboring individual blocks 21 can be reduced when the connecting wire 11 is bent. To "reduce" means that the individual blocks 21 more closely fit with a curve of the connecting wire even though the individual blocks 21 interfere with each other.

Figure 10:
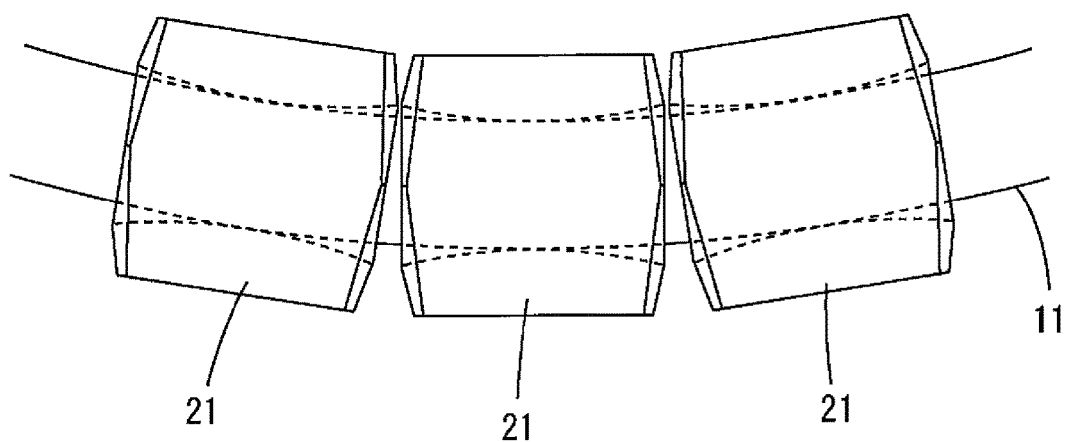
FIG. 10 is a schematic diagram showing interference between neighboring individual blocks when the connecting wire is bent.

FIGS. 10 and 11 schematically show interference between neighboring individual blocks 21 when the connecting wire 11 is bent. In FIGS. 10 and 11, tapered shape is drawn exaggeratingly in order to show an effect clearly. Actually, the tapered shape does not have to be so significant as these figures.

As shown in FIG. 10, by using the individual block 21 whose width is maximum at the center in a longitudinal direction and narrower at a front end and a rear end, the interference between two neighboring individual blocks 21 can be reduced when the connecting wire 11 is bent on an X-Y plane. Similarly, as shown in FIG. 11, the interference between two neighboring individual blocks 21 can be reduced when the connecting wire 11 is bent on an X-Z plane (also on a Y-Z plane).

In addition, the individual blocks 21 are also narrower toward a labial or buccal side, same as a lingual side. This is because the individual blocks 21 can be used without problems even when the front side and the rear side are reversed.

In FIG. 5, an orthodontic bracket 31 is shown. Because the individual block 21 has a polygonal cross-section, the individual block 21 can engage with a concave portion 32 of the orthodontic bracket 31 so as to connect between the individual block 21 and the orthodontic bracket 31.

Figure 6:
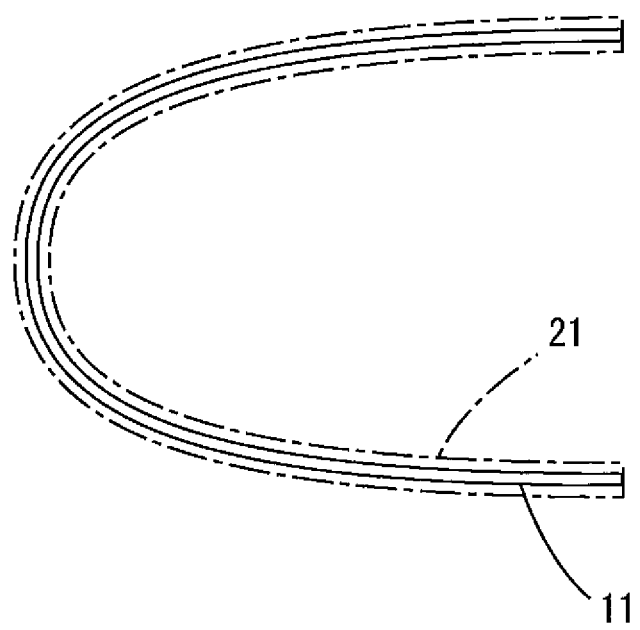
FIG. 6 is a plan view showing an entire shape of the orthodontic arch wire appliance where a connecting wire is inserted into the individual blocks.
Figure 7:
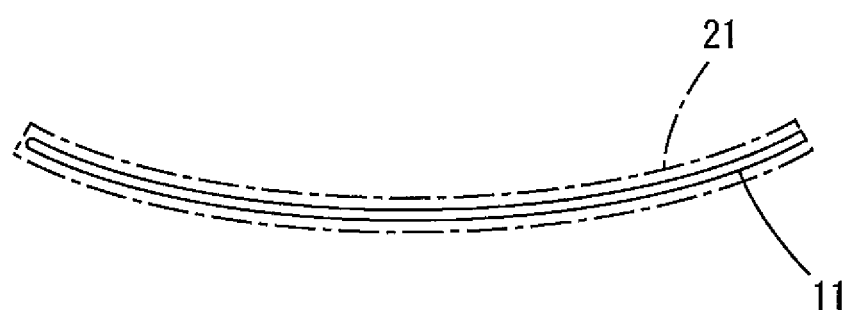
FIG. 7 is a side view of the entire shape.

FIG. 6 shows an entire shape of the orthodontic arch wire appliance in a plan view where a connecting wire is inserted into the individual blocks. FIG. 7 shows it in a side view. Note that the individual blocks 21 are not individually shown on the figure. Instead, the individual blocks 21 are shown by a dashed line to indicate that the individual blocks 21 cover the connecting wire 11 shown by a solid line.

Figure 9:
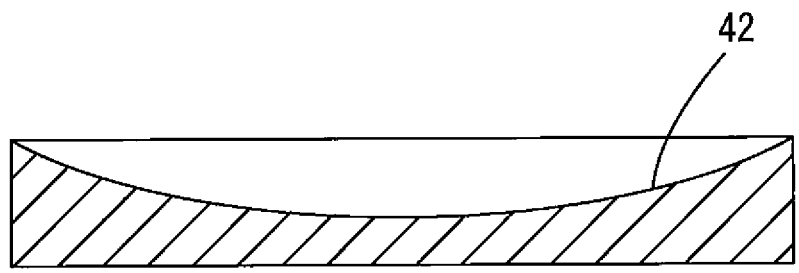
FIG. 9 is a cross-sectional view of a concave Monson spherical plate.

FIGS. 8 and 9 respectively show a convex Monson spherical plate 41 and a concave Monson spherical plate 42 in a cross-sectional view.

Theoretically, the Monson spherical plates 41 and 42 are a portion of a spherical surface having a curvature radius of approximately 10 cm (basic dimension). However, since the curve of the occlusal surface changes due to individual differences such as gender or race, a size of the Monson spherical plates can be variously changed in order to accommodate the individual differences. Although the Monson spherical plate is formed of, for example, metals or plastics (including transparent or semi-transparent plastics) so as to keep a constant shape, deformable materials can be also used so as to match an actual shape of the occlusal surface that changes due to the individual differences.

To enable mass production, the arch wire 11, including the one having a shape of the Monson curve, can be standardized for various sizes to accommodate various sizes (curvature radius) of the Monson spherical plates 41 and 42.

A cross-sectional shape of the connecting wire 11 can be variously set as needed, including circular, square or rectangular cross-sectional shape. A material of the connecting wire 11 can be shape memory alloys such as "True-Chrome" (stainless steel wire) or "Elgiloy" both manufactured by Rocky Mountain Morita Corporation, "Wallaby" or "Azurloy" both manufactured by Ormco Corporation, "Ni—Ti" (nickel-titanium alloy) or "TMA" (titanium molybdenum alloy) both manufactured by Ormco Corporation, or any other materials suitable for dental use.

If an orthodontic bracket having wider concave portion is used instead of the conventional orthodontic bracket 31, relatively large individual blocks 21 can be used without changing the connecting wire 11. Specifications of the connecting wire 11, such as materials, can be selected so as to provide suitable elasticity.

The connecting wire 11 can be a single wire, a multi-strand braided wire made of two or more wires twisted together to form a rectangular cross-section such as "Force 9" manufactured by Ormco Corporation, a wire made of a core wire and two or more wires wound spirally around the core wire, or any other wires suitable for dental use.

If an arch curve (arch form) is previously drawn on the Monson spherical plates 41 and 42, the connecting wire 11 can be formed by being bent along the arch curve. As a result, the connecting wire 11 having a curve corresponding to the curve of the occlusal surface, which is also called as the Monson curve, can be obtained. In addition, the connecting wire 11 can be formed in advance to have a curve corresponding to the spherical surface of the Monson spherical plates 41 and 42, so as to be fit with the curve of the occlusal surface (Monson curve).

The connecting wire 11 having circular cross-section is inserted into the individual blocks 21 in advance, then the connecting wire 11 is bent on the Monson spherical plates 41 and 42 according to the arch form (arch curve), then a torque is applied to the individual blocks 21, and then the connecting wire 11 is fixed by a certain method such as heat, chemistry, electricity or adhesion.

However, the manufacturing method of the orthodontic arch wire appliance is not limited to the above process. Alternatively, the orthodontic arch wire appliance can be manufactured by preliminary inserting a linear shaped connecting wire 11 into the individual blocks 21 to be sold in that state. Alternatively, the orthodontic arch wire appliance can be manufactured by inserting the connecting wire 11 into the individual blocks 21 and then bending the connecting wire 11 along general Monson curve to be sold in that state.

The polygonal cross-section includes a square, a rectangular, a trapezoidal, a parallelogram or other cross-sections. However, the number of surfaces is not limited to four. If the connecting wire 11 has a circular cross-section, each of the individual blocks 21 contacts with the entire surface of connecting wire 11 regardless of an angle of the individual block 21. Therefore, by using the connecting wire 11 having the circular cross-section, a fixing force can be increased.

Figure 12:
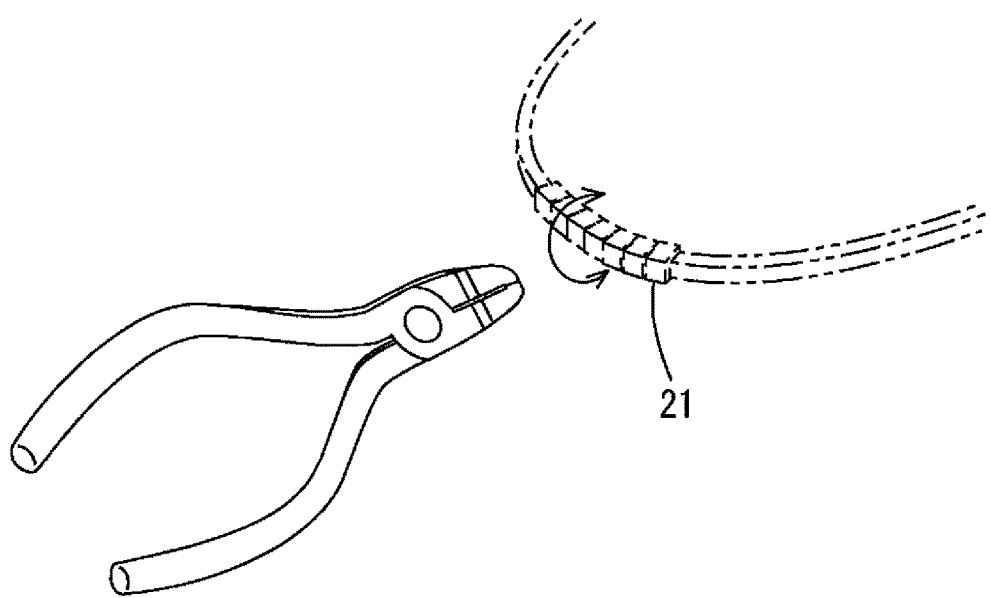
FIG. 12 shows a method for adjusting the orthodontic arch wire appliance.
Figure 13:
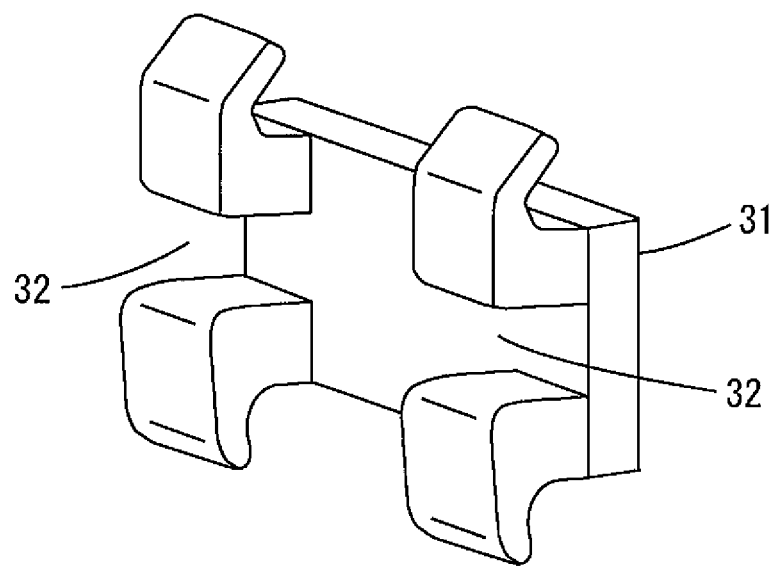
FIG. 13 is a perspective view of an orthodontic bracket.

FIG. 12 shows a method for adjusting the orthodontic arch wire appliance. FIG. 13 shows an orthodontic bracket 31 in a perspective view.

The connecting wire 11 inserted into the individual blocks 21 is formed into a shape of the arch curve on the Monson spherical plate. Then, each of the individual blocks 21 is twisted so as to cause a necessary torque. Because a twist is individually applied to each of the individual blocks 21, a necessary torque can be obtained keeping the three-dimensional curve such as the Monson curve. Because each of the individual blocks 21 is fixed by being inserted into the concave portion 32 of the orthodontic bracket 31, a necessary torque can be applied to the orthodontic bracket 31 by a counter force to release the twist.

By the way, if the shape memory alloy is used, number of times of adjustment can be decreased.

FIG. 14 shows a chart of a combination of materials of the connecting wire and the individual blocks, selecting from a material using shape memory alloy or a material using non shape memory alloy.

Conventionally, the arch wire was integrally formed, and therefore whole the arch wire was shape memory alloy. However, in the present invention, the connecting wire 11 the individual blocks, both of which comprise the arch wire, are separately formed, and therefore both the material using shape memory alloy and the material using non shape memory alloy can be combined.

When using the shape memory alloy, publicly known means and other appropriate means to memory shape can be used according to the feature of the alloy.

Figure 15:
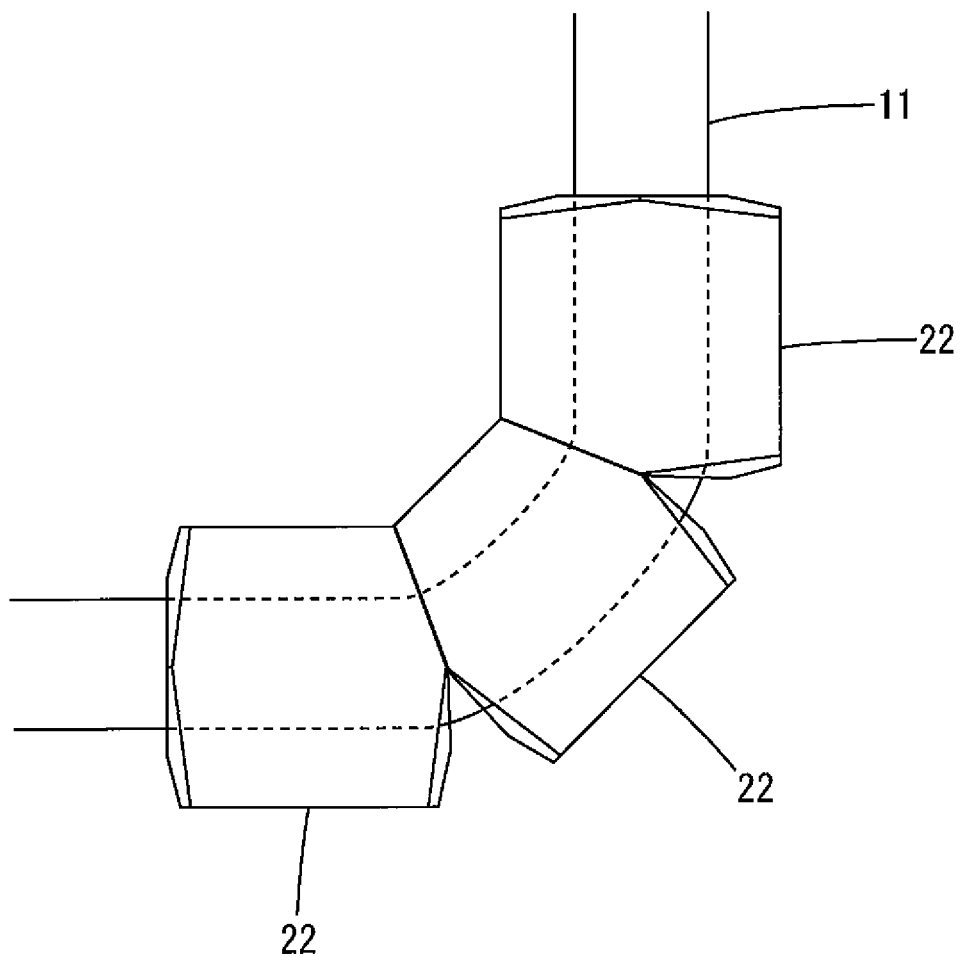
FIG. 15 is a front view of the orthodontic arch wire appliance using an individual block of a variation example.
Figure 16:
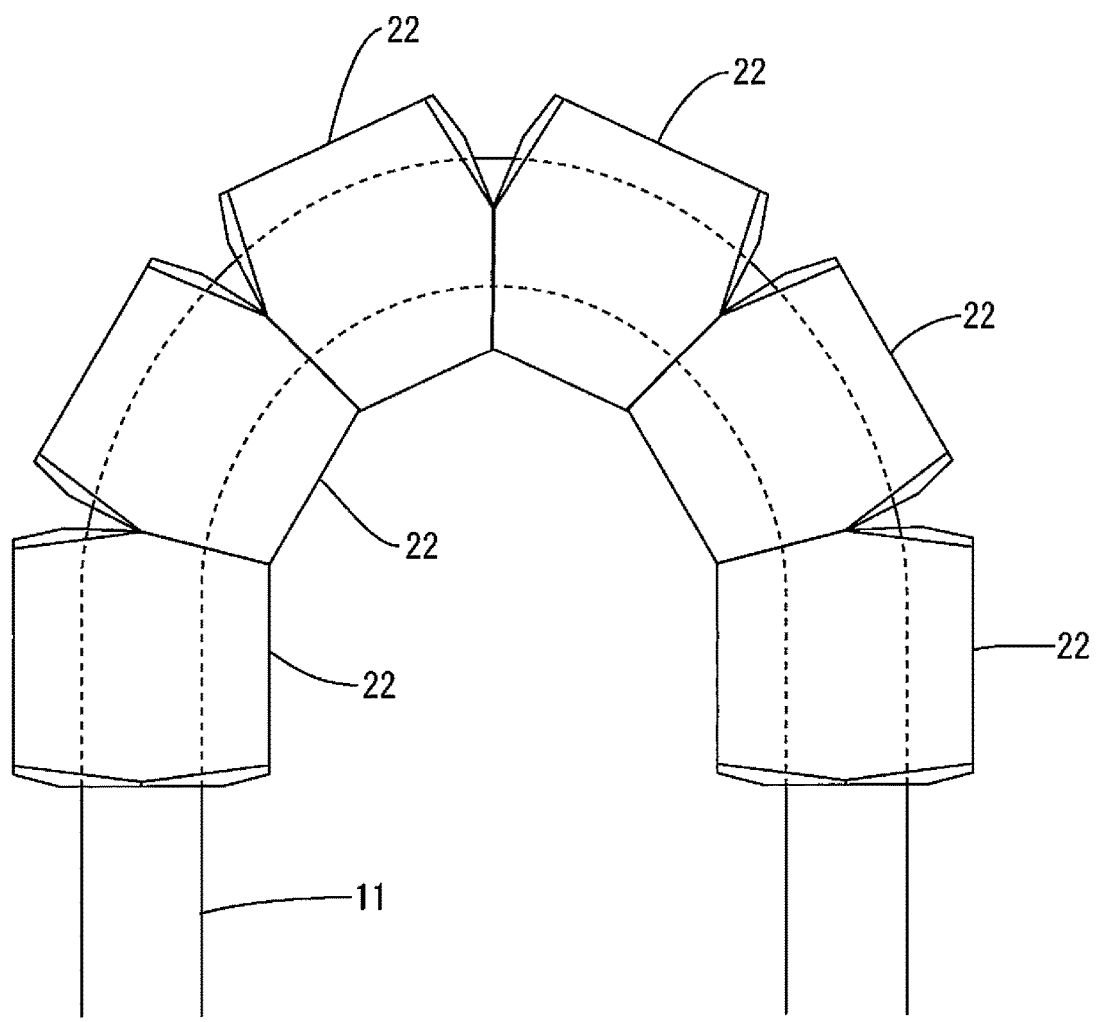
FIG. 16 is a front view of another example of the orthodontic arch wire appliance using the individual block of the variation example.

FIG. 15 shows an orthodontic arch wire appliance using an individual block of a variation example in a front view. FIG. 16 shows another example in a front view.

In the above variation examples, individual blocks 22 are made of a single metal, which is soft and deformable. Specific composition is not disclosed here, but in general, the single metal, which is soft and deformable, can be formed by combining various types of metals. Although the single metal is used in the present embodiment, but a dual structure can be employed such as an inner cylinder and an outer cylinder.

If the arch wire is bent nearly 90 degrees or more than 90 degrees, such as Omega-loop or E-loop shown in FIG. 15, the individual blocks 22 are deformed to match the bent shape of the connecting wire 11. In other words, because the individual blocks 22 are deformed, the arch form of the rectangular arch wire can be formed without displacing the individual blocks 22. Although the individual blocks 22 are deformed, there is no problem no matter how the individual blocks 22 are deformed because the deformed portion is not fit into the orthodontic bracket.

FIG. 16 shows an example of a bull loop. If the arch wire is curved at a top portion, such as the bull top, the individual blocks 22 match the bent shape by displacing their positions. However, it can be also achieved if the individual blocks 22 are deformed.

To fix the individual blocks 21 with the connecting wire 11, various methods can be used such as thermal, chemical or electrical methods. A strong adhesion bond can be also used. The methods for fixing are not limited particularly.

Figure 17:
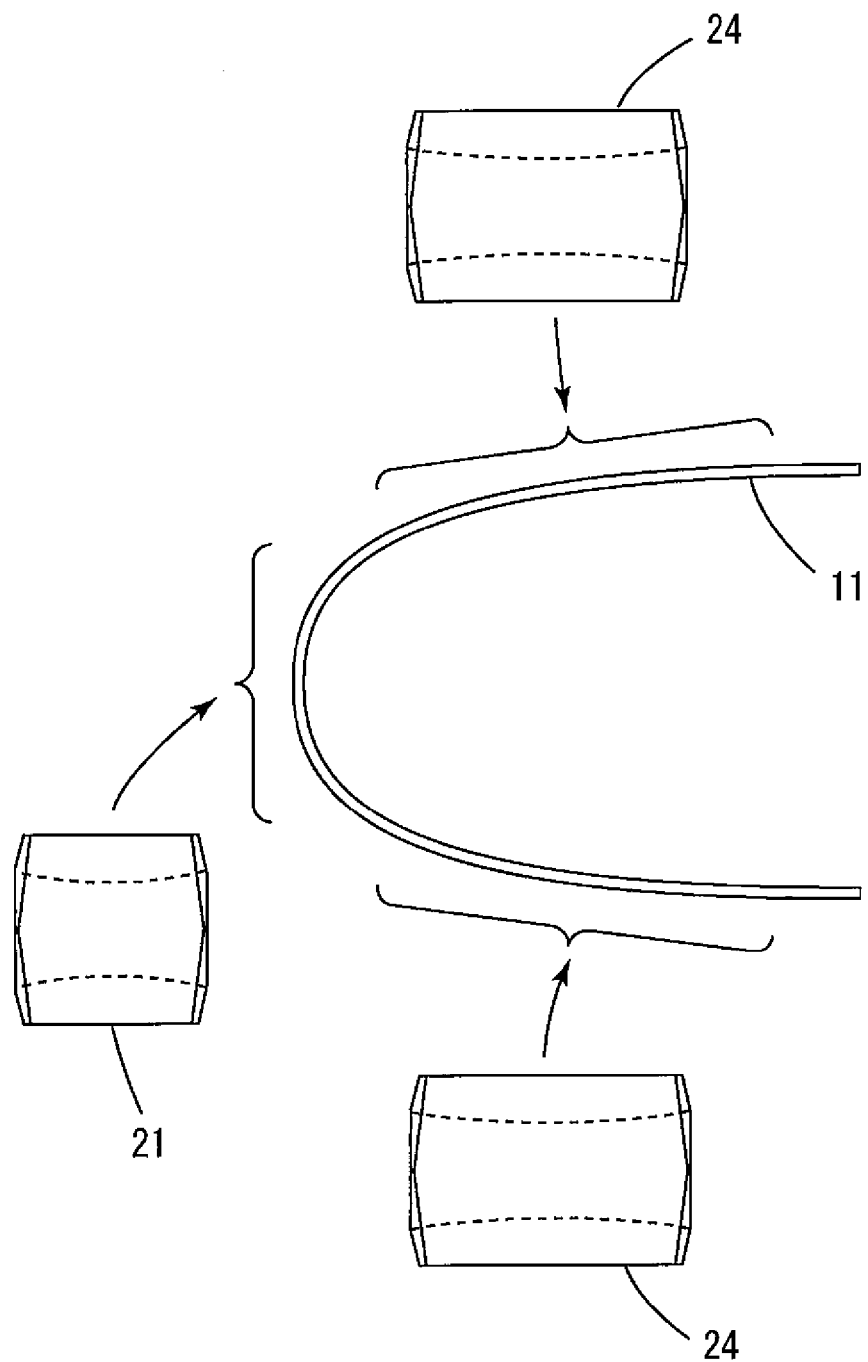
FIG. 17 is a schematic diagram of an example in which individual blocks having different width are used.
Figure 18:
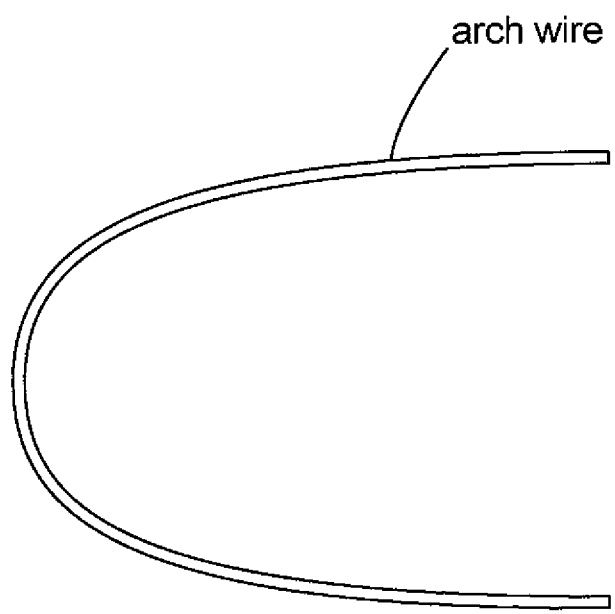
FIG. 18 is a plan view of a conventional arch wire.
Figure 19:
FIG. 19 is a side view of the conventional arch wire.
Figure 20:
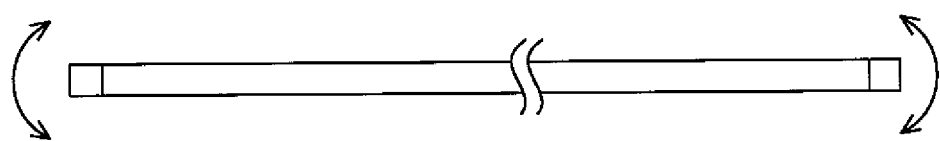
FIG. 20 is a rear view of the conventional arch wire.

FIG. 17 is a schematic diagram of an example in which individual blocks having different width are used.

In addition to the individual blocks 21 which are approximately cubic shapes as previously explained, individual blocks 24 which are one and a half times as wide as the individual blocks 21 can be also used in combination. In other words, as shown in FIG. 17, although the individual blocks 21, which are the cubic shape, are used at a front part of the connecting wire 11 because a curve of the connecting wire 11 is relatively large, individual blocks 24, which is wider than the individual blocks 21, are used at a rear part of the connecting wire 11 because the curve of the connecting wire 11 is relatively small. Consequently, entire the connecting wire 11 can be easily covered by the individual blocks 21 and 24. Of course, the width of the individual blocks 21 and 24 in longitudinal direction can be gradually specified according to the curve of the connecting wire 11 so that the width becomes narrower at a portion where the curve is larger and the width becomes wider at a portion where the curve is smaller.

As explained above, by using the present invention, orthodontic force can be equally applied to each tooth because the teeth are not aligned in a plan view.

Note that, this invention is not limited to the above-mentioned embodiments. Although it is to those skilled in the art, the following are disclosed as the one embodiment of this invention.

Mutually substitutable members, configurations, etc. disclosed in the embodiment can be used with their combination altered appropriately.

Although not disclosed in the embodiment, members, configurations, etc. that belong to the known technology and can be substituted with the members, the configurations, etc. disclosed in the embodiment can be appropriately substituted or are used by altering their combination.

Although not disclosed in the embodiment, members, configurations, etc. that those skilled in the art can consider as substitutions of the members, the configurations, etc. disclosed in the embodiment are substituted with the above mentioned appropriately or are used by altering its combination.

While the invention has been particularly shown and described with respect to preferred embodiments thereof, it should be understood by those skilled in the art that the foregoing and other changes in form and detail may be made therein without departing from the sprit and scope of the invention as defined in the appended claims.

What is claimed is:

1. A rectangular orthodontic arch wire appliance comprising:
   a connecting wire having a circular cross-section; and
   individual blocks having a cross-section configured to engage with an orthodontic bracket and having a through hole extending from a first side surface to a second side surface to insert the connecting wire,
   a top side surface, a bottom side surface, a front side surface, and a rear side surface extending between the first side surface and the second side surface,
   the through hole extending in a longitudinal direction, wherein
   the individual blocks can be fixed to the connecting wire in advance by inserting the connecting wire into the individual blocks,
   each of the individual blocks is contacted with neighboring individual blocks,
   an inner diameter of the through hole is maximum at both the first side surface and the second side surface and the inner diameter becomes gradually smaller toward a center of the through hole so that the connecting wire can be warped in the through hole when the connecting wire is bent, and
   a width of each of the individual blocks is maximum at a center in the longitudinal direction of the individual blocks and narrower at the front side surface or the rear side surface by chamfering corners of both the front side surface and the rear side surface of the individual blocks so that two neighboring individual blocks do not interfere with each other when the connecting wire is inserted into the individual blocks and the connecting wire is bent along a dental arch.

2. The rectangular orthodontic arch wire appliance according to claim 1,
   a vertical direction is transverse to the longitudinal direction
   the width of the individual blocks is maximum at a center in the vertical direction of the individual blocks and narrower at the top side surface or the bottom side surface.

3. The rectangular orthodontic arch wire appliance according to claim 1,
   each of the individual blocks has a hexagonal shape when viewed from the top side surface, the bottom side surface, the front side surface, or the rear side surface.

4. The rectangular orthodontic arch wire appliance according to claim 1, wherein:
   the connecting wire is made of shape memory alloy.

5. The rectangular orthodontic arch wire appliance according to claim 1, wherein:
   the individual blocks are made of shape memory alloy.

6. The rectangular orthodontic arch wire appliance according to claim 1, wherein:

each of the individual blocks is contacted with neighboring individual blocks at the rear side surface of the individual blocks.

\* \* \* \* \*